US011464788B2

(12) United States Patent
Zhang et al.

(10) Patent No.: US 11,464,788 B2
(45) Date of Patent: *Oct. 11, 2022

(54) OLIGOMER-CORTICOSTEROID CONJUGATES

(71) Applicant: Nektar Therapeutics, San Francisco, CA (US)

(72) Inventors: Wen Zhang, San Ramon, CA (US); Jennifer Riggs-Sauthier, Huntsville, AL (US); J. Milton Harris, Huntsville, AL (US); Michael D. Bentley, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 15/788,626

(22) Filed: Oct. 19, 2017

(65) Prior Publication Data

US 2018/0256599 A1    Sep. 13, 2018

Related U.S. Application Data

(63) Continuation of application No. 14/315,998, filed on Jun. 26, 2014, now abandoned, which is a continuation of application No. 12/680,877, filed as application No. PCT/US2008/011523 on Oct. 3, 2008, now Pat. No. 8,796,248.

(60) Provisional application No. 60/997,835, filed on Oct. 5, 2007.

(51) Int. Cl.
*A61K 31/573* (2006.01)
*C07J 41/00* (2006.01)
*A61K 47/60* (2017.01)
*A61K 47/59* (2017.01)

(52) U.S. Cl.
CPC ............ *A61K 31/573* (2013.01); *A61K 47/59* (2017.08); *A61K 47/60* (2017.08); *C07J 41/0005* (2013.01)

(58) Field of Classification Search
CPC .... A61K 31/573; A61K 47/482; A61K 47/59; A61K 47/60; A61P 1/08; A61P 25/00; A61P 25/08; A61P 25/22; A61P 25/24; C07J 41/0005
USPC ................................ 552/653, 518, 577, 274
See application file for complete search history.

(56) References Cited

U.S. PATENT DOCUMENTS

| | | | |
|---|---|---|---|
| 2,403,683 A | 7/1946 | Reichstein | |
| 2,602,769 A | 7/1952 | Murray et al. | |
| 2,789,118 A | 4/1957 | Bernstein et al. | |
| 2,837,464 A | 6/1958 | Nobile | |
| 2,852,511 A | 9/1958 | Fried | |
| 2,897,216 A | 7/1959 | Oliveto et al. | |
| 2,897,218 A | 7/1959 | Sebek et al. | |
| 2,990,401 A | 6/1961 | Bernstein et al. | |
| 3,007,923 A | 11/1961 | Muller et al. | |
| 3,014,938 A | 12/1961 | Mills et al. | |
| 3,031,347 A | 4/1962 | Philipson | |
| 3,038,914 A | 6/1962 | Magerlein et al. | |
| 3,053,865 A | 9/1962 | Taub et al. | |
| 3,104,246 A | 9/1963 | Amiard et al. | |
| 3,124,571 A | 3/1964 | Ringold et al. | |
| 3,126,375 A | 3/1964 | Ringold et al. | |
| 3,225,072 A | 12/1965 | Deghenghi | |
| 3,312,590 A | 4/1967 | Elks et al. | |
| 3,426,128 A | 2/1969 | Kieslich et al. | |
| 3,721,687 A | 3/1973 | Elks et al. | |
| 3,729,495 A | 4/1973 | Kaspar et al. | |
| 3,892,857 A | 7/1975 | Difazio et al. | |
| 3,929,768 A | 12/1975 | Brattsand et al. | |
| 4,076,708 A | 2/1978 | Green et al. | |
| 4,124,707 A | 11/1978 | Green et al. | |
| 4,189,477 A * | 2/1980 | Nedelec | C07J 41/0016 514/182 |
| 4,335,121 A | 6/1982 | Phillipps et al. | |
| 4,472,393 A | 9/1984 | Shapiro | |
| 5,081,111 A | 1/1992 | Akimoto et al. | |
| 5,320,837 A | 6/1994 | Akimoto et al. | |
| 5,672,662 A | 9/1997 | Harris et al. | |
| 5,681,964 A | 10/1997 | Ashton et al. | |
| 6,770,725 B2 | 8/2004 | Santerre | |
| 8,133,977 B2 * | 3/2012 | Bossard | A61K 47/10 530/383 |
| 8,252,275 B2 * | 8/2012 | Bentley | A61K 47/60 424/78.17 |
| 8,354,549 B2 | 1/2013 | Zhang | |
| 8,536,213 B2 * | 9/2013 | Riggs-Sauthier | A61K 47/60 514/390 |

(Continued)

FOREIGN PATENT DOCUMENTS

| | | |
|---|---|---|
| EP | 1 741 434 | 1/2007 |
| WO | WO 02/098949 | 12/2002 |
| WO | WO 2004/052913 | 6/2004 |

OTHER PUBLICATIONS

Abstract of French Patent 2421911 (AN: 1980:426658, HCAPLUS, DN: 93:26658).*
Nedelec, Lucien et al. (Abstract of U.S. Pat. No. 4,189,477: 1979:138097, HCAPLUS, DN: 90:138097).*
Ali-Adib, et al., "Examples of amphitropic polymers: monolayer film, Langmuir-Blodgett film and liquid-crystalline properties of some polymeric amphiphiles containing cholestanol moieties and those of some . . . ", J. Mater. Chem., vol. 6, No. 1, pp. 15-22, (1996).
Chen, et al., "Synthesis and Properties of ABA Amphiphiles", J. Org. Chem., vol. 64, pp. 6870-6873, (1999).

(Continued)

*Primary Examiner* — Sabiha N Qazi
(74) *Attorney, Agent, or Firm* — Jacqueline F. Mahoney

(57) ABSTRACT

The invention provides corticosteroids that are chemically modified by covalent attachment of a water-soluble oligomer. A compound of the invention, when administered by any of a number of administration routes, exhibits a reduced biological membrane crossing rate as compared to the biological membrane crossing rate of the corticosteroid not attached to the water-soluble oligomer.

6 Claims, 1 Drawing Sheet

(56) References Cited

U.S. PATENT DOCUMENTS

| | | | |
|---|---|---|---|
| 8,598,364 | B2 | 12/2013 | Riggs-Sauthier et al. |
| 8,703,878 | B2 | 4/2014 | Kitagawa et al. |
| 8,728,493 | B2 * | 5/2014 | Burton .................... A61P 29/00 424/400 |
| 8,796,248 | B2 * | 8/2014 | Zhang .................. A61K 31/573 514/179 |
| 9,107,956 | B2 | 8/2015 | Riggs-Sauthier et al. |
| 9,725,431 | B2 * | 8/2017 | Zhang .................... C07C 217/48 |
| 10,143,690 | B2 * | 12/2018 | Riggs-Sauthier .... A61K 31/402 |
| 10,265,411 | B2 * | 4/2019 | Riggs-Sauthier .... A61K 31/165 |
| 10,434,181 | B2 * | 10/2019 | Cheng .................. A61K 31/166 |
| 10,463,744 | B2 * | 11/2019 | Riggs-Sauthier ....... A61P 35/00 |
| 2004/0157810 | A1 | 8/2004 | Teicher et al. |
| 2004/0254197 | A1 | 12/2004 | Tasaka et al. |
| 2005/0136031 | A1 | 6/2005 | Bentley et al. |
| 2010/0286107 | A1 | 11/2010 | Zhang et al. |
| 2014/0309398 | A1 | 10/2014 | Zhang et al. |
| 2018/0360979 | A1 * | 12/2018 | Mejia Oneto ...... A61K 47/6939 |

OTHER PUBLICATIONS

Da Han, et al., "Binding of [3H]Triamcinolone Acetonide to Glucocorticoid Receptors in Brain Cytosol Fractions of Rats with Intact Adrenals", Neurochem. Intl., vol. 24, No. 4, pp. 339-348, (1994).

Deng, et al., "Kinetic Evidence for Duplicity in Ion Transport", J. Am. Chem. Soc., vol. 118, pp. 3307-3308, (1996).

Ertl, et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).

Foroutan, et al., "Synthesis and characterisation of polyethylene glycol conjugates of hydrocortisone as potential prodrugs for ocular steroid delivery", Int. J. of Pharma., vol. 157, pp. 103-111, (1997).

Hamed, et al., "Steroidal saponins from the aerial parts of Tribulus pentandrus Forssk", Phytochemistry, vol. 65, pp. 2935-2945, (2004).

Harris, et al., "Laboratory Synthesis of Polyethylene Glycol Derivatives", JMS-REV, Macromol. Chem. Phys., vol. C25, No. 3, pp. 325-373, (1985).

Harris, et al., "Effect of Pegylation on Pharmaceuticals", Nature, vol. 2, pp. 214-221, (Mar. 2003).

Kelder, et al., "Polar Molecular Surface as a Dominating Determinant for Oral Absorption and Brain Penetration of Drugs", Pharmaceu. Res., vol. 16, No. 10, pp. 1514-1519, (1999).

Khandare, et al., "Synthesis, Cellular Transport, and Activity of Polyamidoamine Dendrimer-Methylprednisolone Conjugates", Bioconjugate Chem., vol. 16, pp. 330-337, (2005).

Lebeau, et al., "Synthesis of New Phospholipids Linked to Steroid-Hormone Derivatives Designed for Two-Dimensional Crystallization of Proteins", Helvetica Chimica Acta, vol. 74, pp. 1697-1706, (1991).

Nakagawa, et al., "Synthesis of water-soluble derivatives of sparingly soluble medicinal compounds", Yakugaku Zasshi Journal, Shionogi & Co., Amagasaki, vol. 79, pp. 591-594, (1959).

Vicent, et al., "21-Hydroxy-6, 19-oxidoprogesterone: A Novel Synthetic Steroid with Specific Antiglucocorticoid Properties in the Rat", Mol. Pharmacol., vol. 52, pp. 749-753, (1997).

Zalipsky, "Functionalized Poly(ethylene glycol) for Preparation of Biologically Relevant Conjugates", Bioconjugate Chem., vol. 6, pp. 150-165, (1995).

Abstract of GB Patent 772,166-(AN 1957:86109, Zcaplus, DN 51:86109, Publication date (Apr. 10, 1957).

PCT International Search Report corresponding to PCT International Application No. PCT/US2008/011523 dated Sep. 30, 2009.

PCT International Preliminary Report on Patentability corresponding to PCT International Application No. PCT/US2008/011523 date of issuance of report dated Apr. 7, 2010.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005—2006).

NOF Corporation, PEG Derivatives, Phospholipid and Drug Delivery Materials for Pharmaceuticals, 46 pages, Catalogue 2003-1$^{st}$, (Jan. 2003).

NOF Corporation, PEG Derivatives, Phospholipid and Drug Delivery Materials for Pharmaceuticals, 27 pages, Catalogue 2003-2$^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

POLYPURE Products, PEG amines; PEG acids and amino acids; PEG thiols and disulfides; BIOTINS, 5 pages, (Apr. 2004).

POLYPURE Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producerand provider of monodisperse discrete PEG™ (dPEG™) derivatives, (Product Catalog), 26 pages, (Updated: Jul. 18, 2005).

Quanta Biodesign, Ltd., Leading innovator, producerand provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

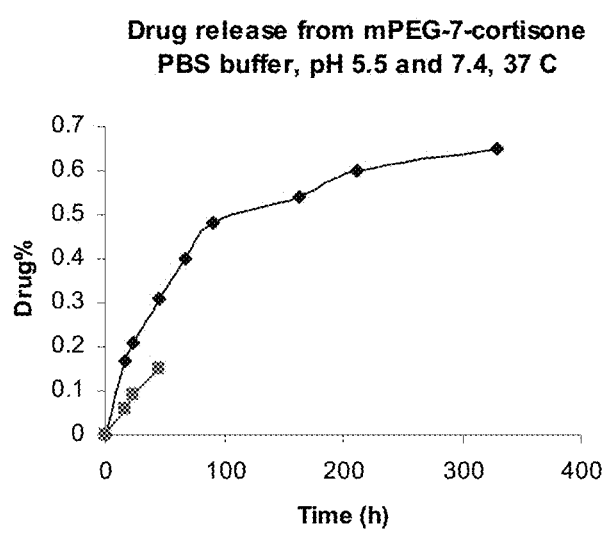

OLIGOMER-CORTICOSTEROID CONJUGATES

CROSS REFERENCE TO RELATED APPLICATION

This application is a continuation of U.S. patent application Ser. No. 14/315,998, filed Jun. 26, 2014, which is a continuation of U.S. patent application Ser. No. 12/680,877, filed Jun. 18, 2010, now U.S. Pat. No. 8,796,248, which is a 35 U.S.C. § 371 application of International Application No. PCT/US2008/011523, filed Oct. 3, 2008, designating the United States, which claims the benefit of priority under 35 U.S.C. § 119(e) to U.S. Provisional Patent Application No. 60/997,835, filed Oct. 5, 2007, all of which are incorporated herein by reference in their entireties.

FIELD OF THE INVENTION

This invention comprises (among other things) chemically modified corticosteroids that possess certain advantages over corticosteroids lacking the chemical modification. The chemically modified corticosteroids described herein relate to and/or have application(s) in (among others) the fields of drug discovery, pharmacotherapy, physiology, organic chemistry and polymer chemistry.

BACKGROUND OF THE INVENTION

Corticosteroids represent a broad class of agents employed in the treatment of individuals suffering from a variety of disorders. In the treatment of an individual suffering from arthritis, for example, administration of a corticosteroid may reduce inflammation. In addition, individuals suffering autoimmune disorders often benefit from the administration of a corticosteroid. Other applications in which corticosteroids have been used include the treatment of individuals suffering from allergic reactions, ankylosing spondylitis, asthma, Crohn's disease dermatological disorders and psoriasis among others. As a class, corticosteroids represent an important and widely used tool in pharmacotherapy.

Although corticosteroids serve an important role in treating patients, their use is sometimes associated with (among other things) CNS side effects, such as insomnia, euphoria, mood changes, nervousness, personality changes, depression, nausea, headaches and convulsions.

As a consequence, pharmacotherapy with corticosteroids would be improved if these and/or other side effects associated with their use could be decreased.

The present invention seeks to address these and other needs in the art.

SUMMARY OF THE INVENTION

In one or more embodiments of the invention, a compound is provided, the compound comprising a corticosteroid residue covalently attached via a hydrazone linkage to a water-soluble, non-peptidic oligomer.

In one or more embodiments of the invention, a compound is provided, the compound comprising a corticosteroid residue covalently attached via a hydrazone linkage to a water-soluble, non-peptidic oligomer, wherein the weight average molecular weight of the water-soluble, non-peptidic oligomer is less than 400 Daltons.

In one or more embodiments of the invention, a compound is provided, the compound comprising a corticosteroid residue covalently attached (either directly or through one or more atoms) at a position other than through the 16 or 17 positions to a water-soluble, non-peptidic oligomer.

In one or more embodiments of the invention, a compound is provided, the compound comprising a corticosteroid residue covalently attached (either directly or through one or atoms) at a position other than through D-ring atom positions to a water-soluble, non-peptidic oligomer.

In one or more embodiments of the invention, a compound is provided, the compound comprising a corticosteroid residue covalently attached (either directly or through one or more atoms) at a position selected from the consisting of A-ring atom positions, B-ring atom positions, and C-ring atom positions to a water-soluble, non-peptidic oligomer.

In one or more embodiments of the invention, a compound is provided, the compound comprising a corticosteroid residue covalently attached (either directly or through one or more atoms) at A-ring atom positions to a water-soluble, non-peptidic oligomer.

In one or more embodiments of the invention, a compound is provided, the compound comprising a corticosteroid residue covalently attached at the 3 position to a water-soluble, non-peptidic oligomer.

Exemplary compounds of the invention include those having the following structure:

(Formula I-C)

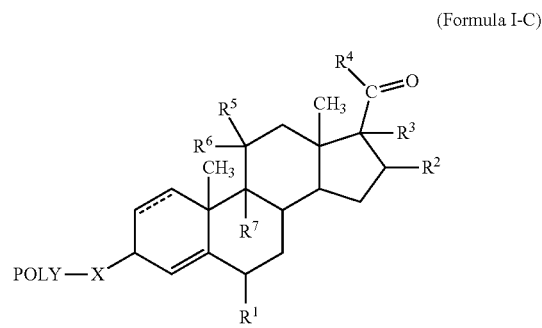

wherein:
the dashed line independently represents an optional double bond;
$R^1$ is selected from the group consisting of halo (e.g., fluoro, chloro, bromo, iodo) and alkyl;
either
$R^2$ is selected from the group consisting of hydroxy and alkyl and $R^3$ is selected from the group consisting of hydroxy, alkyl, —OC(O)-alkyl, and —OC(O)-cyclo, or
$R^2$ and $R^3$ combine to form a moiety selected from the group consisting of

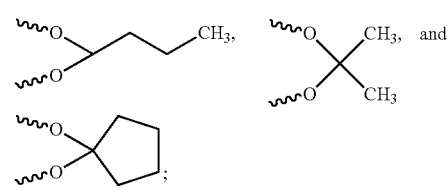

$R^4$ is selected from the group consisting of —$CH_3$, —$CH_2$—OH, —$CH_2$-halo, —S—$CH_2$-halo, —$CH_2$—O—C(O)—$CH_3$, —$CH_2$—O—C(O)—$CH_2$—$CH_3$, —$CH_2$—$PO_4$, —$CH_2$—O—C(O)—C(CH_3)_3$, —CH$_2$—O—C(O)—CH$_2$—CH$_2$—CH$_2$—CH$_3$, —CH$_2$—C(O)—O—CH$_3$, —CH$_2$—O—C(O)—CH$_2$—CH$_2$—C(O)—OH;

either

R$^5$ is —H and R$^6$ is selected from the group consisting of —H and hydroxy, or R$^5$ and R$^6$ combine to form carbonyl;

R$^7$ is halo;

X is a spacer moiety; and

POLY is a water-soluble, non-peptidic oligomer.

The "corticosteroid residue" is a compound having a structure of a corticosteroid that is altered by the presence of one or more bonds, which bonds serve to attach (either directly or indirectly) one or more water-soluble, non-peptidic oligomers. In this regard, any compound having corticosteroid activity can be used. Exemplary corticosteroids have a structure encompassed by the structure defined herein as Formula I:

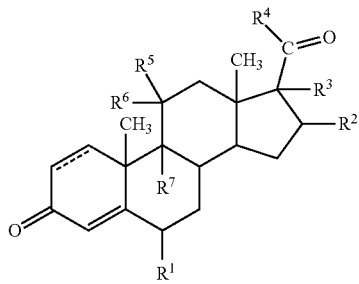

(Formula I)

wherein:

the dashed line independently represents an optional double bond;

R$^1$ is selected from the group consisting of halo (e.g., fluoro, chloro, bromo, iodo) and alkyl;

either R$^2$ is selected from the group consisting of hydroxy and alkyl and R$^3$ is selected from the group consisting of hydroxy, alkyl, —OC(O)-alkyl, and —OC(O)-cyclo, or R$^2$ and R$^3$ combine to form a moiety selected from the group consisting of

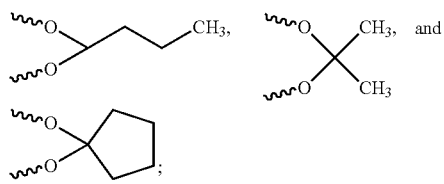

R$^4$ is selected from the group consisting of —CH$_3$, —CH$_2$—OH, —CH$_2$-halo, —S—CH$_2$-halo, —CH$_2$—O—C(O)—CH$_3$, —CH$_2$—O—C(O)—CH$_2$—CH$_3$, —CH$_2$—PO$_4$, —CH$_2$—O—C(O)—C(CH$_3$)$_3$, —CH$_2$—O—C(O)—CH$_2$—CH$_2$—CH$_2$—CH$_3$, —CH$_2$—C(O)—O—CH$_3$, —CH$_2$—O—C(O)—CH$_2$—CH$_2$—C(O)—OH;

either R$^5$ is —H and R$^6$ is selected from the group consisting of —H and hydroxy, or R$^5$ and R$^6$ combine to form carbonyl; and R$^7$ is halo.

In one or more embodiments of the invention, a composition is provided, the composition comprising a compound comprising a corticosteroid residue covalently attached via a stable or degradable linkage to a water-soluble and non-peptidic oligomer, and optionally, a pharmaceutically acceptable excipient.

In one or more embodiments of the invention, a dosage form is provided, the dosage form comprising a compound comprising a corticosteroid residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a corticosteroid.

In one or more embodiments of the invention, a method is provided, the method comprising administering a compound comprising a corticosteroid residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

BRIEF DESCRIPTION OF THE DRAWING

FIG. 1 is a drawing presenting results obtained in connection with Example 3.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 95% (by weight), in water at room temperature. An unfiltered aqueous preparation of a "water-soluble" oligomer transmits at least 75%, more preferably at least 95%, of the amount of light transmitted by the same solution after filtering. On a weight basis, a "water soluble" oligomer is preferably at least 35% (by weight) soluble in water, more preferably at least 50% (by weight) soluble in water, still more preferably at least 85% (by weight) soluble in water. It is preferred, however, that the water-soluble oligomer is at least 95% (by weight) soluble in water or completely soluble in water.

The terms "monomer," "monomeric subunit" and "monomeric unit" are used interchangeably herein and refer to one of the basic structural units of a polymer or oligomer. In the case of a homo-oligomer, this is defined as a structural repeating unit of the oligomer. In the case of a co-oligomer, a monomeric unit is more usefully defined as the residue of a monomer which was oligomerized to form the oligomer, since the structural repeating unit may include more than one type of monomeric unit. Preferred oligomers are homo-oligomers.

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention may comprise the following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Branched", in reference to the geometry or overall structure of an oligomer, refers to an oligomer having two or more polymer "arms" extending from a branch point.

"Forked" in reference to the geometry or overall structure of an oligomer, refers to an oligomer having two or more functional groups (through one or more atoms) extending from a branch point.

A "branch point" refers to a bifurcation point comprising one or more atoms at which an oligomer branches or forks from a linear structure into one or more additional arms.

The terms "reactive" and "activated" refer to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the corticosteroid residue. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the corticosteroid residue. A composition comprised of bimodal conjugates may, however, include one or more nonconjugate substances such as solvents, reagents, excipients, and so forth.

A "corticosteroid" refers to an organic, inorganic, or organometallic compound having a molecular weight of less than about 1000 Daltons and having some degree of corticosteroid activity. Corticosteroid activity can be measured by art-known methods. For example, corticosteroid activity can be measured by testing male Sprague-Dawley rats by injecting a relatively large amount (e.g., 5-20 mg/kg) of the compound of interest into an animal. After three days, the thymus glands can be removed and weighed using the procedure described in Vicent et al. (1997) *Mol. Pharmacol.* 52:749-753.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or can be determined by one of ordinary skill in the art. Preferably, a conjugate of the invention can provide a reduced rate of metabolism reduction satisfying at least one of the following values: at least about 5%; at least about 15%; at least about 20%; at least about 25%; at least about 30%; at least about 40%; at least about 60%; at least about 70%, at least about 80%, and at least about 90%.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Electrophile" refers to an ion, atom, or an ionic or neutral collection of atoms having an electrophilic center, i.e., a center that is electron seeking, capable of reacting with a nucleophile.

"Nucleophile" refers to an ion or atom or an ionic or neutral collection of atoms having a nucleophilic center, i.e., a center that is seeking an electrophilic center, and capable of reacting with an electrophile.

"Pharmaceutically acceptable excipient" or "pharmaceutically acceptable carrier" refers to component that may be included in the compositions of the invention and that causes no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a corticosteroid residue covalently attached via a stable or degradable linkage to a water-soluble, non-peptidic oligomer.

In one or more embodiments of the invention, a compound is provided, the compound comprising a corticosteroid residue covalently attached via a stable or degradable linkage to a water-soluble, non-peptidic oligomer, wherein the corticosteroid has a structure encompassed by the following formula:

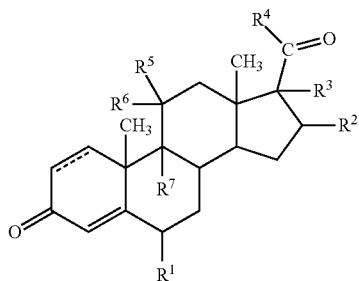

(Formula I)

wherein:

the dashed line independently represents an optional double bond;

$R^1$ is selected from the group consisting of halo (e.g., fluoro, chloro, bromo, iodo) and alkyl;

either $R^2$ is selected from the group consisting of hydroxy and alkyl and $R^3$ is selected from the group consisting of hydroxy, alkyl, —OC(O)-alkyl, and —OC(O)-cyclo, or $R^2$ and $R^3$ combine to form a moiety selected from the group consisting of

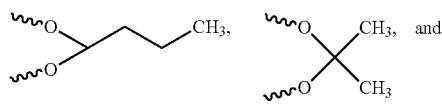

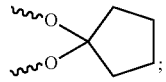

$R^4$ is selected from the group consisting of —$CH_3$, —$CH_2$—OH, —$CH_2$-halo, —S—$CH_2$-halo, —$CH_2$—O—C(O)—$CH_3$, —$CH_2$—O—C(O)—$CH_2$—$CH_3$, —$CH_2$—$PO_4$, —$CH_2$—O—C(O)—C($CH_3$)$_3$, —$CH_2$—O—C(O)—$CH_2$—$CH_2$—$CH_2$—$CH_3$, —$CH_2$—C(O)—O—$CH_3$, —$CH_2$—O—C(O)—$CH_2$—$CH_2$—C(O)—OH;

either $R^5$ is —H and $R^6$ is selected from the group consisting of —H and hydroxy, or $R^5$ and $R^6$ combine to form carbonyl; and $R^7$ is halo.

Examples of specific corticosteroids include those selected from the group consisting of desoxycorticosone, hydrocortisone, cortisone, methylprednisolone, prednisone, prednisolone, triamcinolone, dexamethasone, betamethasone, beclomethasone, beclomethasone-17,21-dipropionate, budesonide, flunisolide, fludrocortisone, mometasone, fluticasone, alclometasone, clocortolone, flurandrenolide, fluocinonide, hydrocortisone acetate, fluorometholone, fluocinolone acetonide, diflucortolone valerate, paramethasone acetate, halcinonide, hydrocortisone phosphate, clobetasone butyrate, amcinonide, and prednisolone succinate.

As used herein, the conventional ring atom numbering system for identifying positions of atoms and rings within a corticosteroid will be used, as follows:

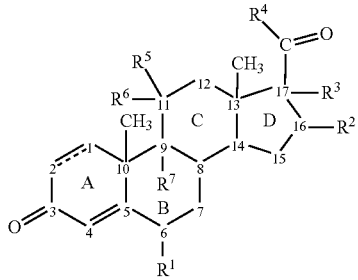

(Formula I)

One of ordinary skill in the art will readily determine the positions of atoms and rings of the corresponding corticosteroid residue. When referring to positions of attachment, it will be understood that when a given moiety is stated to be attached at a certain numbered position or a position within a ring it can be either direct (i.e., directly to one of the ring atoms numbered 1 through 17) or indirect (i.e., one or more atoms linking the moiety to one of the ring atoms numbered one 1 through 17). As used herein, the first numbered ring atom to which a given moiety is attached determines that moiety's attachment site. Thus, a corticosteroid residue attached in accordance with Formula I-C is only considered attached to an oligomer at the 3-position, and not (for example) attached to the 2 position by way of the ring atom at the 3-position.

Use of discrete oligomers (e.g., from a monodisperse or bimodal composition of oligomers, in contrast to relatively impure compositions) to form oligomer-containing compounds can advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability can be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in blood-brain barrier crossing rate for a conjugate of the invention is at least about 20%.

As indicated above, the compounds of the invention include a corticosteroid residue. Assays for determining whether a given compound (regardless of whether the compound includes a water-soluble, non-peptidic oligomer or not) act as a corticosteroid are described herein.

In one or more embodiments, the corticosteroid is one of the following corticosteroids:

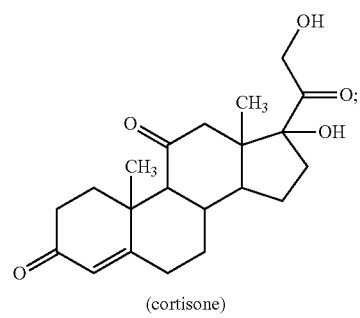

(cortisone)

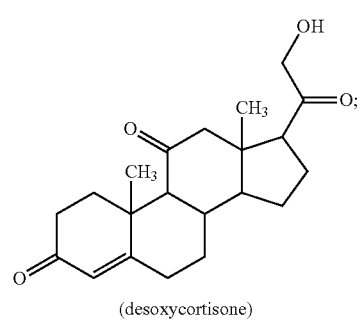

(desoxycortisone)

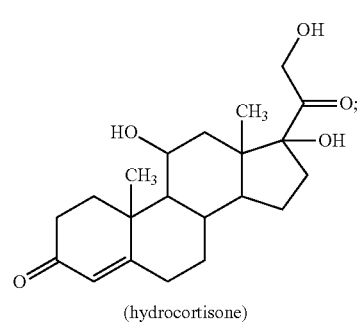

(hydrocortisone)

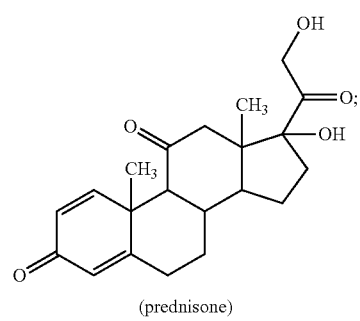

(prednisone)

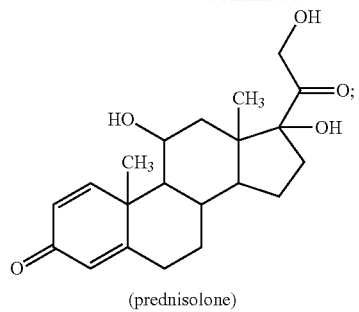
(prednisolone)
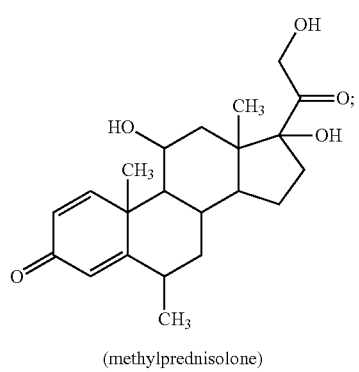
(methylprednisolone)
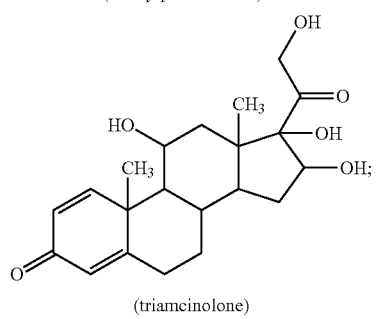
(triamcinolone)
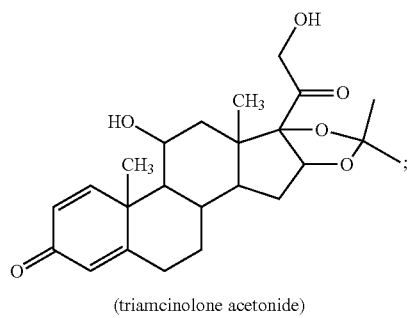
(triamcinolone acetonide)
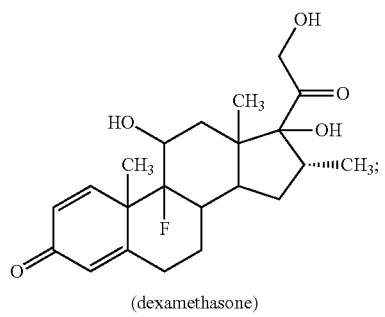
(dexamethasone)
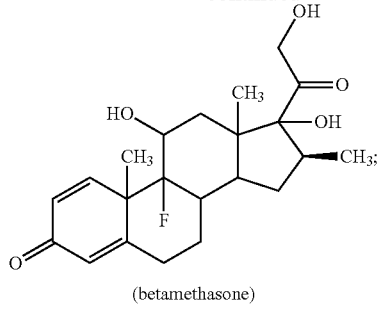
(betamethasone)
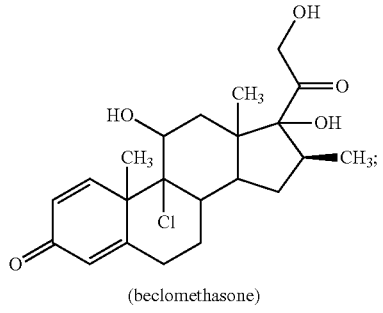
(beclomethasone)
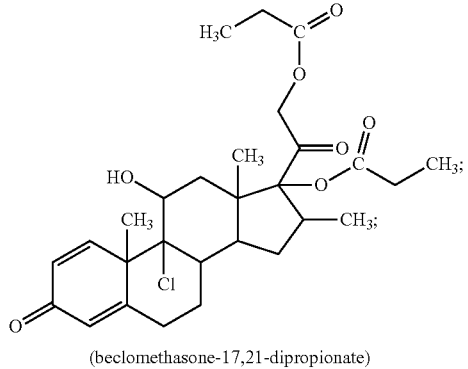
(beclomethasone-17,21-dipropionate)
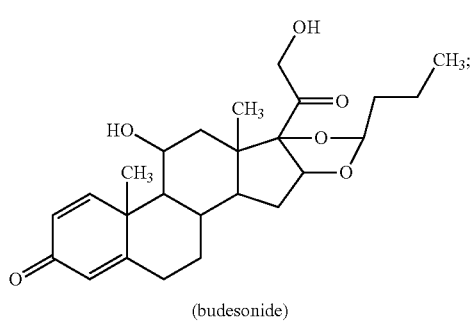
(budesonide)
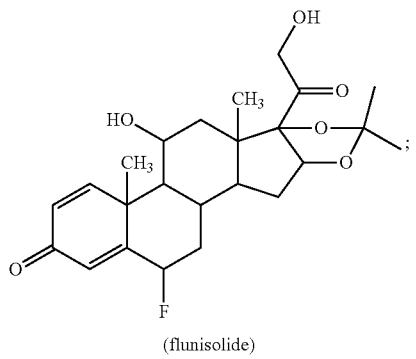
(flunisolide)

-continued
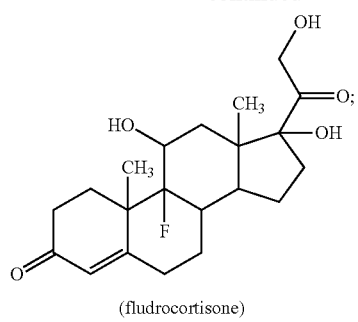
(fludrocortisone)
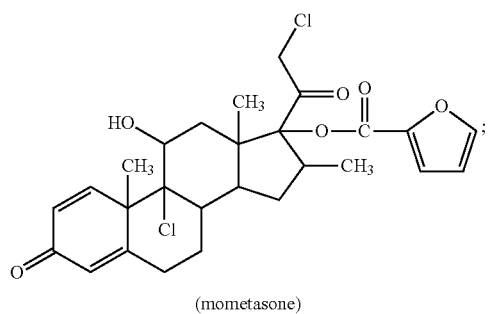
(mometasone)
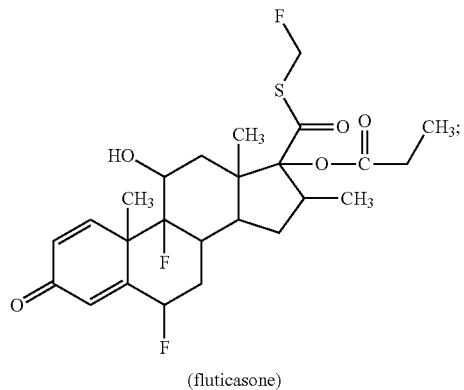
(fluticasone)
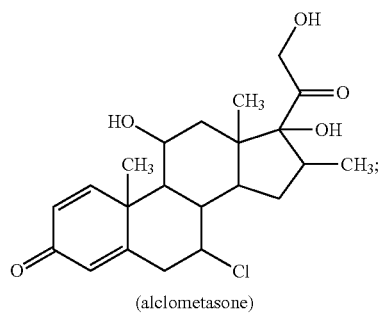
(alclometasone)
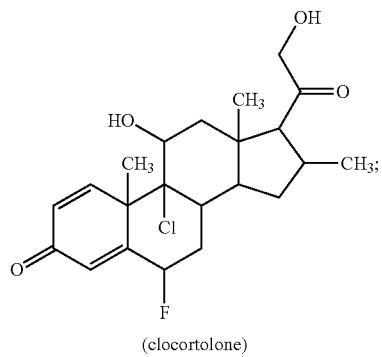
(clocortolone)
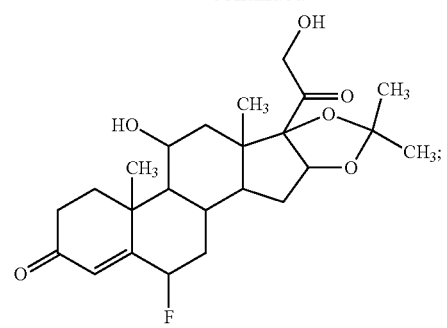
(flurandrenolide)
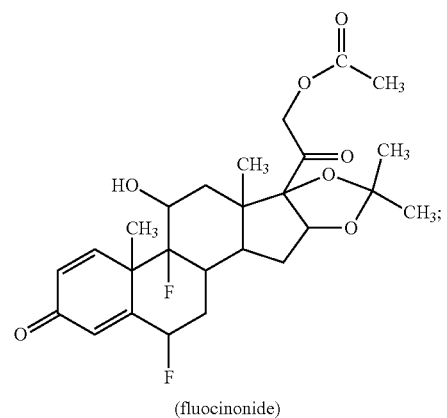
(fluocinonide)
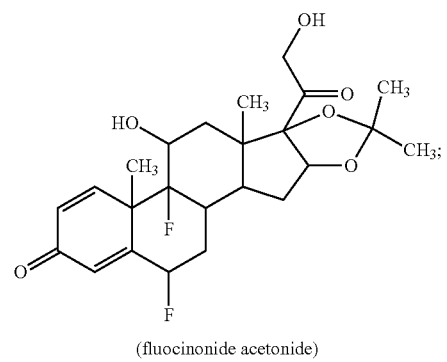
(fluocinonide acetonide)
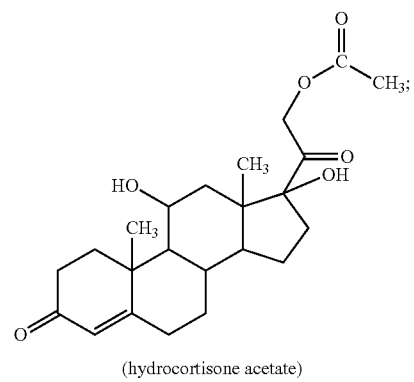
(hydrocortisone acetate)

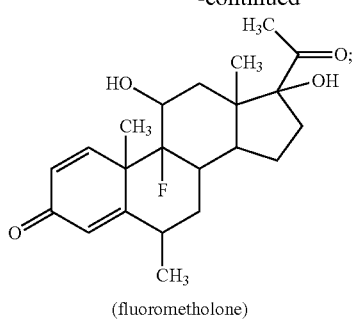
(fluorometholone)

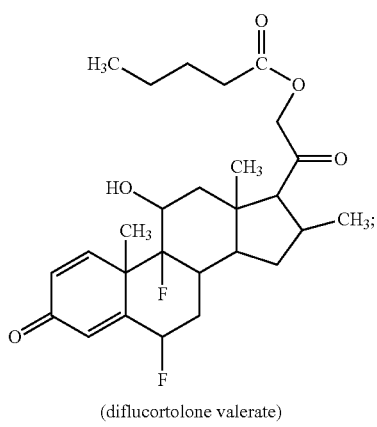
(diflucortolone valerate)

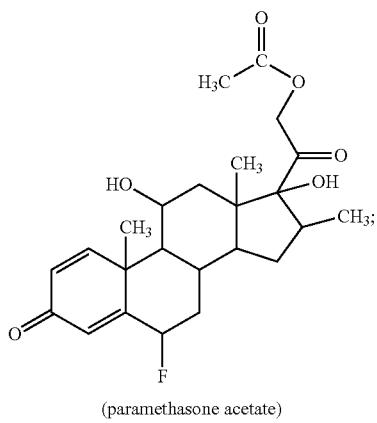
(paramethasone acetate)

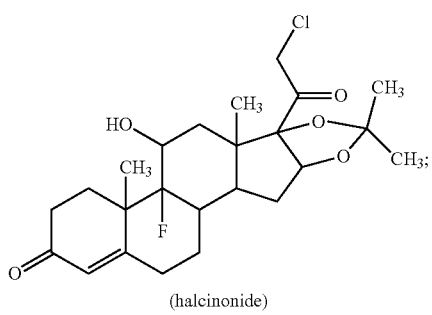
(halcinonide)

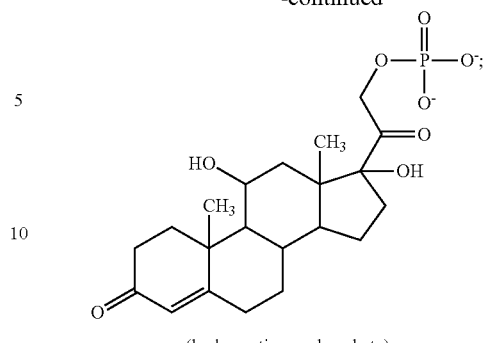
(hydrocortisone phosphate)

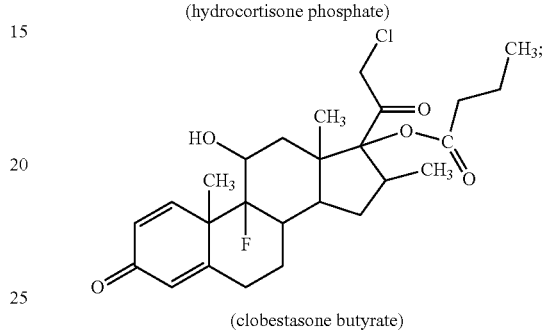
(clobestasone butyrate)

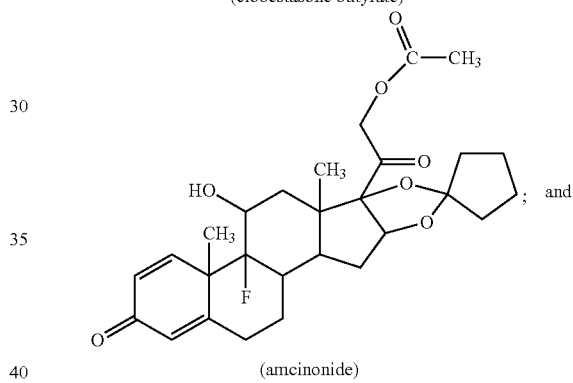
; and (amcinonide)

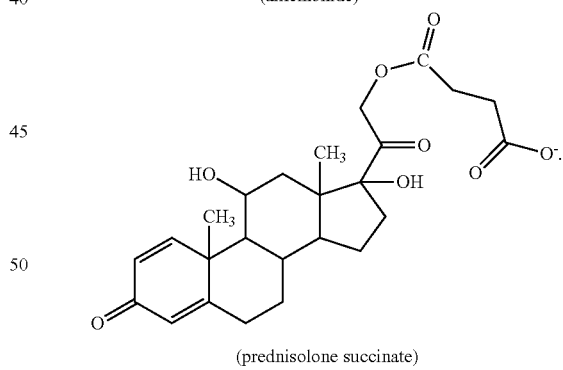
(prednisolone succinate)

In some instances, corticosteroids can be obtained from commercial sources. In addition, corticosteroids can be obtained through chemical synthesis. Examples of corticosteroids as well as synthetic approaches for preparing corticosteroids are described in the literature and in, for example, U.S. Pat. No. 2,403,683 (cortisone and others); U.S. Pat. No. 2,602,769 (hydrocortisone and others); U.S. Pat. No. 2,897,216 (prednisone and others); U.S. Pat. No. 2,837,464 (prednisolone and others); U.S. Pat. No. 2,897,218 (methylprednisolone and others); U.S. Pat. Nos. 2,789,118 and 3,031,347 (triamcinolone and others); U.S. Pat. No. 2,990,401 (triamcinolone acetonide and others); U.S. Pat. No. 3,007, 923 (dexamethasone and others); U.S. Pat. Nos. 3,053,865 and 3,104,246 (betamethasone and others); U.S. Pat. No. 3,312,590 (beclomethasone and others); U.S. Pat. No. 3,929,768 (budesonide and others); U.S. Pat. No. 2,852,511 (fludrocortisone and others); U.S. Pat. No. 4,472,393 (mometasone and others); U.S. Pat. No. 4,335,121 (fluticasone and others); U.S. Pat. Nos. 4,076,708 and 4,124,707 (alclometasone and others); U.S. Pat. No. 3,729,495 (clocortolone and others); U.S. Pat. No. 3,126,375 (flurandrenolide and others); U.S. Pat. No. 3,124,571 (fluocinonide and others); U.S. Pat. No. 3,014,938 (fluocinonide acetonide and others); U.S. Pat. No. 2,602,769 (hydrocortisone and others); U.S. Pat. No. 3,038,914 (fluorometholone and others); U.S. Pat. No. 3,426,128 (diflucortolone and others); U.S. Pat. No. 3,892,857 (halcinonide and others); and U.S. Pat. No. 3,721,687 (clobetasone and others). In addition, salts and esters of a corticosteroid can also be used so long as the oligomer-containing compound retains at least some degree of corticosteroid activity.

Each of these (and other) corticosteroids can be covalently attached (either directly or through one or more atoms) to a water-soluble and non-peptidic oligomer.

Exemplary molecular weights of small molecule drugs include molecular weights of: less than about 950; less than about 900; less than about 850; less than about 800; less than about 750; less than about 700; less than about 650; less than about 600; less than about 550; less than about 500; and less than about 450.

The small molecule drug used in the invention, if chiral, may be obtained from a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The corticosteroid for coupling to a water-soluble, non-peptidic oligomer possesses a free hydroxyl, carboxyl, thio, amino group, or the like (i.e., "handle") suitable for covalent attachment to the oligomer. In addition, the corticosteroid can be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the corticosteroid (in contrast to the step-wise addition of one or more monomers to effectively "grow" the oligomer onto the corticosteroid), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the corticosteroid) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the corticosteroid residue and the water-soluble, non-peptidic oligomer), —O—, —NH—, —S—, —C(O)—, C(O)—NH, NH—C(O)—NH, O—(O)—NH, —OC(O)—NH—N=, =N—NH—C(O)O—, —C(O)—NH—N=, =N—NH—C(O)—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the corticosteroid) with a corresponding functional group within the corticosteroid. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O—(CH_2—CH_2—O)_n—(CH_2)_p—C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The terminus of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the corticosteroid may not have a functional group suited for conjugation. In this instance, it is possible to modify (or "functionalize") the "original" corticosteroid so that it does have a functional group suited for conjugation. For example, if the corticosteroid has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule corticosteroid bearing a carboxyl group wherein the carboxyl group-bearing small molecule corticosteroid is coupled to an amino-terminated oligomeric ethylene glycol, to provide a conjugate having an amide group covalently linking the small molecule corticosteroid to the oligomer. This can be performed, for example, by combining the carboxyl group-bearing small molecule corticosteroid with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule corticosteroid bearing a hydroxyl group wherein the hydroxyl group-bearing small molecule corticosteroid is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule corticosteroid bearing a ketone group by first reducing the ketone group to form the corresponding hydroxyl group. Thereafter, the small molecule corticosteroid now bearing a hydroxyl group can be coupled as described herein.

In still another example, it is possible to prepare a conjugate of a small molecule corticosteroid bearing a carbonyl group by using hydrazono-de-oxo-substitution. In one approach, a carbonyl group-bearing small molecule corticosteroid (such as a ketone group-bearing corticosteroid) and a hydrazine-bearing oligomer are dissolved in a suitable buffer and allowed to react, thereby forming a hydrazone-containing linkage between the corticosteroid residue and the oligomer.

In still another instance, it is possible to prepare a conjugate of a small molecule corticosteroid bearing an amine group. In one approach, the amine group-bearing small molecule corticosteroid and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule corticosteroid and the carbonyl carbon of the aldehyde-bearing oligomer.

In another approach for preparing a conjugate of a small molecule corticosteroid bearing an amine group, a carboxylic acid-bearing oligomer and the amine group-bearing small molecule corticosteroid are combined, typically in the presence of a coupling reagent (e.g., DCC). The result is an amide linkage formed between the amine group of the amine group-containing small molecule corticosteroid and the carbonyl of the carboxylic acid-bearing oligomer.

An exemplary conjugate of the invention is provided below having the following structure:

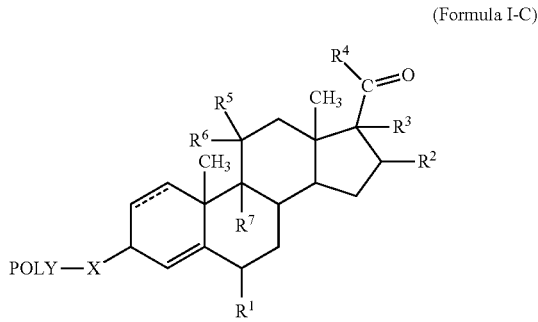

(Formula I-C)

wherein:
the dashed line represents an optional double bond;
$R^1$ is selected from the group consisting of halo and alkyl;
either
$R^2$ is selected from the group consisting of hydroxy and alkyl and $R^3$ is selected from the group consisting of hydroxy, alkyl, —OC(O)-alkyl, and —OC(O)-cyclo, or
$R^2$ and $R^3$ combine to form a moiety selected from the group consisting of

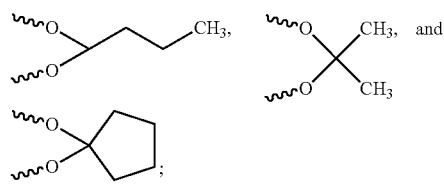

$R^4$ is selected from the group consisting of —CH$_3$, —CH$_2$—OH, —CH$_2$-halo, —S—CH$_2$-halo, —CH$_2$—O—C(O)—CH$_3$, —CH$_2$—O—C(O)—CH$_2$—CH$_3$, —CH$_2$—PO$_4$, —CH$_2$—O—C(O)—C(CH$_3$)$_3$, —CH$_2$—O—C(O)—CH$_2$—CH$_2$—CH$_2$—CH$_3$, —CH$_2$—C(O)—O—CH$_3$, —CH$_2$—O—C(O)—CH$_2$—CH$_2$—C(O)—OH;
either
$R^5$ is —H and $R^6$ is selected from the group consisting of —H and hydroxy, or
$R^5$ and $R^6$ combine to form carbonyl;
$R^7$ is halo;
X is a spacer moiety; and
POLY is a water-soluble, non-peptidic oligomer.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the corticosteroid or the conjugate of a corticosteroid and a water-soluble non-peptidic polymer has activity as a corticosteroid, it is possible to test such a compound. Such methods are known to those of ordinary skill in the art and described herein.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by an NMR spectrometer manufactured by Bruker. A list of certain compounds as well as the source of the compounds is provided below.

Example 1

Preparation of Hydrazine-Bearing Oligomers

Hydrazine-bearing oligomers (a type of oligomeric reagent) were prepared following the schematic provided below.

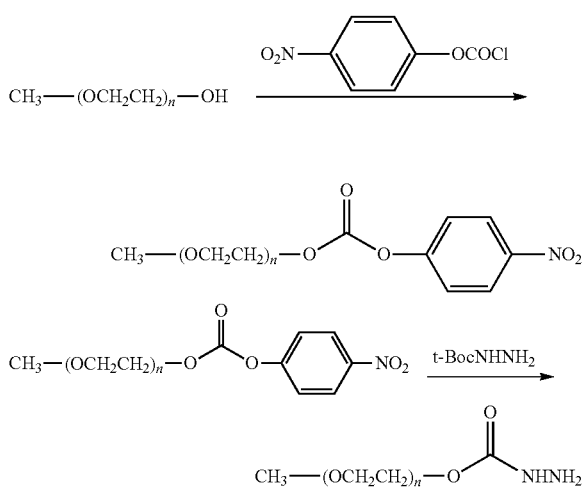

$CH_3$—$(OCH_2CH_2)_n$—OH (1.0 mmol) and DMAP (1.5 mmol) were dissolved in 20 ml DCM to form a solution. To the solution, 4-nitrophenyl chlorformate (1.0 mmol) was added. The reaction mixture was stirred overnight at room temperature. t-Butyl carbazate (2.0 mmol) was added into the mixture which was then stirred for additional 24 hours at room temperature. DCM (150 ml) was added into the mixture and the DCM phase was washed with water (150 ml×2) and then dried. The crude product was deprotected by DCM/TFA (2:1). The solvent and TFA were removed, and the residue was dissolved in 200 ml DCM, which was washed with 5% $Na_2CO_3$ and water. After removing solvent and drying, the product (a hydrazine-bearing oligomer reagent) was obtained as an oil, which could be used in a coupling reaction.

Using this approach, hydrazine-bearing oligomeric reagents wherein n is 3, 7 and 8 were made.

Example 2

Coupling Reaction

Using hydrazine-bearing oligomers prepared in accordance with Example 1, conjugates were prepared following the schematic below.

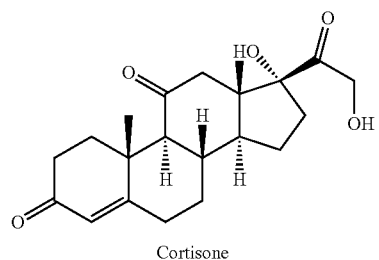
Cortisone

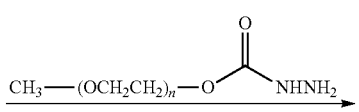

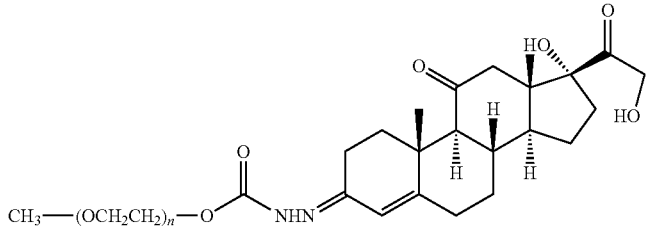

The corticosteroid, cortisone, (1.0 mmol) and a hydrazine-bearing oligomer prepared in accordance with Example 1, (1.5 mmol) were dissolved in 10 ml CH$_3$OH to form a solution. To the solution, 5 drops of acetic acid were added. The reaction mixture was stirred overnight at room temperature. DCM (150 ml) was added into the mixture. The DCM phase was washed with 1% Na$_2$CO$_3$ and then with water (150 ml×2). After dried and removing the solvent, the crude product was purified by silicon gel column (DCM: MeOH, 20:1). The products were obtained as solid or sticky oil (yield: ~70-90%, purity: 92-99%).

To conjugate dexamethasone, the same process is generally followed except that dexamethasone is used in place of cortisone and the reaction is run at reflux in methanol for three days.

Using this approach, hydrazine-bearing oligomeric reagents wherein n was 3 was made for hydrocortisone ("mPEG$_3$-Hydrocortisone") and dexamethasone ("mPEG$_3$-Dexamethasone"), wherein n was 7 was made for hydrocortisone ("mPEG$_7$-Hydrocortisone"), cortisone ("mPEG$_7$-Cortisone") and dexamethasone ("mPEG$_7$-Dexamethasone"), and wherein n was 8 was made for hydrocortisone ("mPEG$_8$-Hydrocortisone"), cortisone ("mPEG$_8$-Cortisone") and dexamethasone ("mPEG$_8$-Dexamethasone").

Example 3

Hydrolysis Testing mPEG$_7$-Cortisone prepared in accordance with Example 2 (n in the oligomer equal to seven) were tested for hydrolysis at pH 5.5 and 7.4. The drug was stable and the conjugate was able to release cortisone clearly at pH 5.5. The cortisone release from the compound at pH 7.4 is much slower than that at pH 5.5. However, many decomposed impurities from cortisone were observed with extended time at pH 7.4. Hydrocortisone is much more stable than cortisone in PBS buffer at pH 7.4.

A graph of the results is provided in FIG. 1.

Example 4

Glucocorticoid Binding Assay

The assay was used to determine whether the tested compounds bound to the glucocorticoid binding site and is based on procedures set forth in the literature. See, for example, Da Han et al. (1994) Neurochem. Int. 24:339-348. Briefly, using competitive binding of with the radioligand "[6,7-$^3$H]triamcinolone acetonide" (30-50 Cl/mmol), reactions were carried out in 50 mM KH$_2$PO$_4$ (pH 7.4) containing 10 mM sodium molybdate and 10 mM α-monothioglycerol at 0° C. for 16 hours. The glucocorticoid receptors were obtained from rat brains. The reactions were terminated by rapid vacuum filtration onto glass fiber filters. Radioactively trapped onto the filters is determined and compared to control values. The IC$_{50}$ value, or the half maximal inhibitory concentration, represents the concentration of a test compound that is required for 50% displacement of the radioligand from the receptor. A higher IC$_{50}$ value reflects a weaker binding affinity. The IC$_{50}$ values for several compounds prepared in accordance with Example 3 as well as some oligomer-free corticosteroids are presented in Table 1.

TABLE 1

IC$_{50}$ Values for Tested Compounds

| Drug | IC$_{50}$ (M) |
|---|---|
| Triamcinolone Acetonide | $1.21 \times 10^{-9}$ |
| Cortisone | $3.89 \times 10^{-6}$ |
| mPEG$_7$-Cortisone | $3.44 \times 10^{-6}$ |
| Hydrocortisone | $3.62 \times 10^{-8}$ |
| mPEG$_7$-Hydrocortisone | $3.93 \times 10^{-9}$ |
| Dexamethasone | $1.50 \times 10^{-9}$ |
| mPEG$_7$-Dexamethasone | $7.93 \times 10^{-7}$ |

What is claimed is:

1. A compound having the structure:

[Chemical structure shown with steroid core bearing OH, CH3, HO, CH3, OH, CH3, F substituents, connected via POLY—O—C(=O)—N(H)—N= linkage]

wherein POLY is a poly(alkylene oxide) having a number of repeating monomers in the range of from 2 to 30.

2. The compound of claim 1, wherein the poly(alkylene oxide) is a poly(ethylene oxide).

3. The compound of claim 1, wherein the poly(alkylene oxide) has a number of repeating monomers in the range of from 2 to 10.

4. The compound of claim 1, wherein the poly(alkylene oxide) includes an alkoxy or hydroxy end-capping moiety.

5. A composition comprising the compound of claim 1 and a pharmaceutically acceptable excipient.

6. A composition comprising the compound of claim 1, wherein the compound is present in a dosage form.

* * * * *